United States Patent [19]

Zaiger et al.

[11] Patent Number: Plant 7,474

[45] Date of Patent: Mar. 19, 1991

[54] PLUM TREE "GOLDEN GLOBE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 416,667

[22] Filed: Oct. 2, 1989

[51] Int. Cl.[5] ..... A01H 5/00

[52] U.S. Cl. ..... Plt./38

[58] Field of Search ..... Plt./38

*Primary Examiner*—Howard J. Locker

[57] ABSTRACT

A new and distinct variety of plum tree which has the following unique combination of desirable features:

1. Vigorous upright growth.
2. Regular and productive bearer of large size fruit.
3. Bearing fruit with good flavor and eating quality.
4. Fruit is nearly uniform in size throughout the tree.
5. Fruit with good storage and shipping quality.

1 Drawing Sheet

ORIGIN OF THE VARIETY

The new variety of plum tree was originated by us in our experimental orchard located at Modesto, Calif. from a cross between Laroda Plum (non-patented) and Queen Ann Plum (non-patented). A large number of seedlings were grown under careful observation and one such seedling was expecially desirable with respect to its fruit characteristics and was selected for reproduction and commercialization.

ASEXUAL REPRODUCTION OF THE VARIETY

The present variety of plum tree was asexually reproduced by budding as performed by us in our experimental orchard located at Modesto, Calif. and shows that all said characteristics run true to the original tree and are established and transmitted through succeeding propagations.

SUMMARY OF THE VARIETY

This new and distinct variety of plum tree is of large size, vigorous upright growth and is a regular and productive bearer of nearly uniform large size fruit. The fruit is further characterized by having nearly uniform maturity, being very round in shape, having good flavor and eating quality, an attractive yellow skin color and the ability to ship to long distance markets.

DESCRIPTION OF THE PHOTOGRAPHS

The accompanying photographs show typical specimens of the foliage and fruit of the present plum variety. The illustrations show a branch with the upper and lower surface of the leaves and specimens of the fruit with the exterior skin color and a sectional view of the fruit being divided in the suture plane showing flesh color with the stone remaining in place. The illustrations were taken shortly after the fruit was picked at maturity (shipping ripe) and the colors are as nearly true as is reasonably possible in a color representation of this type.

DESCRIPTION OF THE VARIETY

The following is a detailed botanical description of the new and distinct plum tree, its fruit, flowers and foliage as based on observations of specimens grown at Modesto, Calif., two color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Shape.*—Pruned to vase form.
- *Production.*—Productive.
- *Bearing.*—Regular.

Trunk:
- *Size.*—Large.
- *Texture.*—Shaggy.
- *Color.*—Brown to soot brown — (5-F-5) to (5-F-7).

Branches:
- *Size.*—Medium.
- *Texture.*—Rough to medium rough.
- *Lenticels.*—Large size. Numerous.

*Color.*—New growth — brown to leather brown — (6-E-4) to (6-E-6). Old growth — brown to grayish brown — (6-F-4) to (6-F-6).

Leaves:

*Size.*—Large. Average length — 3½" to 4½". Average width — 1½" to 2".

*Texture.*—Smooth.

*Petiole.*—Average length — ¾". Average width — 1/16".

*Glands.*—Number varies from 1 to 4. Average number 2. Globose. Usually located on base of leaf blade.

*Margin.*—Serrate.

*Shape.*—Oblanceolate. Tip — acuminate.

*Color.*—Upper surface — green to dark green (28-F-6) to (28-F-8). Lower surface — green to grayish green (28-E-5) to (28-E-6).

Flower buds:

*Size.*—Small to medium.

*Length.*—Medium.

*Shape.*—Medium to short. Plump.

Flowers:

*Blooming period.*—Date of first bloom: Feb. 27, 1987. Date of full bloom: Mar. 3, 1987.

*Color.*—White.

*Size.*—Medium.

Fruit:

*Maturity when described.*—Firm ripe.

*Date of first picking.*—July 31, 1987.

*Date of last picking.*—Aug. 6, 1987.

*Size.*—Large. Average diameter axially — 2½". Average transversely in suture plane — 2½".

*Form.*—Globose. Nearly symmetrical.

*Suture.*—Very shallow — nearly smooth, extends from base to apex.

*Cavity.*—Rounded to very slightly elongated in suture plane. Average depth — ½". Average breadth — ½".

*Base.*—Nearly rounded to slightly retuse.

*Apex.*—Nearly rounded.

*Stem.*—Average length — ½". Average width — 3/32".

Flesh:

*Ripens.*—Evenly.

*Texture.*—Firm.

*Eating quality.*—Good.

*Flavor.*—Mild — sub-acid.

*Juice.*—Moderate.

*Color.*—Light yellow to yellow (3-A-7) to (4-A-6).

Skin:

*Thickness.*—Medium.

*Texture.*—Medium — tenacious to flesh.

*Tendency to crack.*—None.

*Down.*—Wanting.

*Color.*—Yellow to oliver yellow — (2-A-8) to (2-C-8).

Stone:

*Type.*—Clingstone.

*Size.*—Small. Average length — ¾". Average width — ⅝". Average thickness — ⅜".

*Apex.*—Usually rounded. Varies from rounded to slight point.

*Base.*—Usually straight. Varies from straight to slightly rounded.

*Surface.*—Irregularly pitted throughout.

*Tendency to split.*—None.

*Color.*—Light brown to brownish orange (6-C-5) to (6-C-6).

Use: Dessert. Local and long distance market.

Keeping quality: Good.

Shipping quality: Good.

The present variety of plum tree, its foliage and fruit herein described, as grown under the ecological conditions prevailing at Modesto, Calif., may vary in slight detail due to climatic conditions, soil type and cultural practices under which the variety may be grown.

We claim:

1. A new and distinct variety of plum tree, substantially as illustrated and described, characterized by its large size, vigorous upright growth and being a regular and productive bearer of large, firm, yellow flesh, clingstone fruit with good flavor and eating quality; the fruit of which is further characterized by being nearly uniform in size throughout the tree and having good shipping and storage quality.

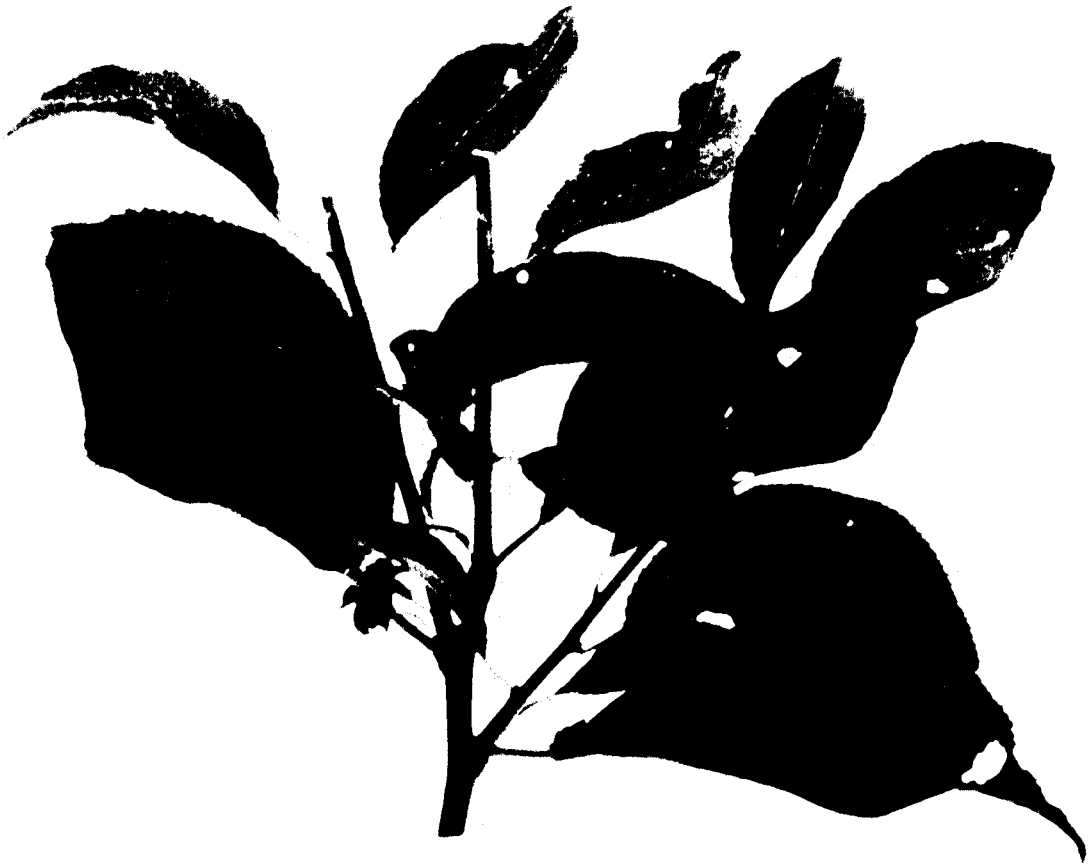

* * * * *